United States Patent [19]

Rysanek et al.

[11] 4,225,820

[45] Sep. 30, 1980

[54] APPARATUS FOR DIAGNOSING MILK SECRETION DISORDERS IN ANIMALS

[75] Inventors: Dušon Ryšánek; Bohumír Kotrč, both of Brno; Jaroslaw Hamalčik, Pelhrimov; Peter Olejník, Brno, all of Czechoslovakia

[73] Assignee: Vyzkumny ustav veterinarniho lekarstvi, Brno, Czechoslovakia

[21] Appl. No.: 8,570

[22] Filed: Feb. 1, 1979

[30] Foreign Application Priority Data

Feb. 3, 1978 [CS] Czechoslovakia ............... 673-78

[51] Int. Cl.² ............................................. G01N 27/07
[52] U.S. Cl. ................................. 324/450; 73/61 R; 73/425.4 R; 422/74
[58] Field of Search ..................... 324/450, 446, 439; 73/53, 61 R, 425.4 R; 422/74

[56] References Cited

U.S. PATENT DOCUMENTS

| 3,250,118 | 5/1966 | Johnson | 73/53 |
| 3,485,086 | 12/1969 | Roman | 73/61 R |
| 3,841,756 | 10/1974 | Grochowicz | 324/439 X |
| 3,878,831 | 4/1975 | Zackheim | 422/74 X |

Primary Examiner—Harold A. Dixon
Assistant Examiner—Charles F. Roberts

[57] ABSTRACT

There is disclosed an apparatus for diagnosing milk secretion disorders in animals such as cows. The apparatus is based upon an electric detection of deviations from the properties of a standard milk secretion, and comprises a holder carrying a diagnostic dish divided by partition walls into a number of diagnostic units corresponding to the number of teats of the animal. The diagnostic units are each provided with a measuring probe exposed to the mouths of scavenging nozzles and with a circuit for evaluating the milk quality as by its electrical conductivity. The outlet of said circuit is connected to the inlet of a display indicating, for example, when the quality of the milk in each diagnostic unit exceeds a predetermined value.

5 Claims, 3 Drawing Figures

APPARATUS FOR DIAGNOSING MILK SECRETION DISORDERS IN ANIMALS

The present invention relates to an apparatus for diagnosing disorders in the secretion of initial milk emission of an animal milked off before applying a milking unit. The operation of the apparatus is based upon the electrical detection of deviations from the properties of a standard milk.

An important step in machine milking, which has an essential diagnostic significance, is milking off the initial milk emission. In this step, a milker determines whether it is or is not allowable to empty the respective mammary gland by means of the milking machine. In this way it is possible to find animals with an ill gland or glands, to exclude them from the herd to be machine milked, and to subject them to further diagnostic or, if necessary, veterinary medical treatments.

The afore-mentioned step has hitherto been carried out by visually examining the initial milk emission milked off into a special vessel designed for this purpose. Because of its subjectivity, however, such method of examination is far from being reliable. An ill cow may escape detection and then be milked by a milking machine. On the one hand, the respective teat cup may be contaminated with germs which have caused an inflammatory disease and, on the other hand, the milk from such animal is unsuitable as a nutritive substance for man. Apart from this, the germs can be transferred to other animals, thus contributing to the propagation of infections of infectious mastitis types. Thus the entire batch of raw milk from a herd, if containing a relatively large proportion of defective milk, loses its nutritive value and the quality necessary for an acceptable dairy process. In this manner, considerable economical losses occur.

In some known methods it has been attempted to diagnose milk secretion disorders during the milking process proper, particularly by means of diagnostic sensors disposed at various points along the channels for withdrawing milk from the teats. Such methods, however, are subject to many problems, so that they have failed in practice. The principal difficulty is in that the signalling of a secretion disorder is too late when the teat cups have been contaminated and a batch of milk has already been spoiled by defective milk. Apart from this, the use of signalling during the milking process lays extraordinary claims on the milker, diverts his attention from the work, and impairs thus his labor routine. The diagnostic efficiency of an apparatus with sensors disposed in the common channel for withdrawing milk from the fore udder of a cow, for example, is very low. The installation of sensors in each individual milking unit is rather uneconomical because of the large number of sensors. Because of the time required for the maintenance or adjustment of the individual diagnostic units, such a practice is very expensive and moreover raises the probability of failure. The aforementioned disadvantages are further multiplied when the sensors are installed in each teat cup.

The present invention provides an apparatus for diagnosing milk secretion disorders, which eliminates the disadvantages of the prior art as hereinabove set forth.

The apparatus in accordance with the invention comprises a holder carrying a diagnostic dish divided by partition walls into diagnostic units. The diagnostic units are provided with measuring probes exposed to the mouths of scavenging nozzles and with signal lights interconnected in a circuit for evaluating the milk quality, the output of said circuit being connected to the inlet of a display showing the diagnostic results of the tests on milk from the udder then under test. The holder can be embodied as a handle receiving a scavenging liquid supply, as well as conductors for supplying power to the measuring probes and to the signal lights.

In accordance with another feature of the invention, the measuring probes are located in respective bottom parts of the diagnostic units, while the scavenging nozzles are situated in a body disposed between the measuring probes and connected via a valve to the scavenging liquid supply. To facilitate the manipulation, the valve is preferably embodied as a hose valve controlled by a hand lever.

Another feature of the invention is that the milk quality evaluating circuit is parallel-connected with a circuit for monitoring measuring probes for measuring the degree of filling of each unit with milk, the last-mentioned circuit comprising a display showing the total number of examinations.

The apparatus of the invention makes it possible to achieve a substantially higher efficiency in obtaining information about the capability of individual mammary glands of an animal, i.e. teats, to be emptied by a milking machine. Moreover, the apparatus enables such information to be acquired at the most convenient instant of the milking process whereby the milker's work is made easier and better. The operation of the apparatus makes it further possible to prevent the teat cups of the milking unit from being contaminated and to reduce thus the transfer of bacterial germs causing infectious material of the contagious mastitis types. Apart from this, any degradation of milk by modified secretions is also prevented. The apparatus further decreases the necessity of labor to be expended upon the maintenance and adjustment of the diagnostic units. The prime cost as well as the rate of failure of the apparatus are relatively low. Finally, the apparatus makes it possible to attain a quite new effect consisting in the automatic scoring of the number of examinations of mammary glands in relation to the number of glands suffering from a secretion disorder, and particularly in every milking process. This offers the possibility of automatically checking every day on the condition of the individual mammary glands of animals in a herd, as well as the milking procedure employed by a milker.

A preferrred embodiment of the apparatus according to the present invention will hereinafter be described with reference to the accompanying drawings which, however, are not intended to limit in any way the scope of the invention.

Figure 1:
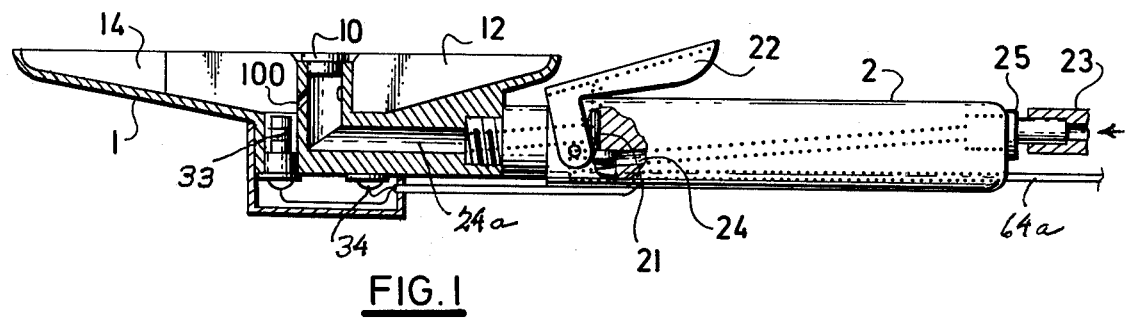
FIG. 1 is a view partially in elevation and partially in longitudinal section taken alon line 1-1 of FIG. 2 of the portion of the apparatus incorporating the diagnostic units.

As can be seen in the drawings, and particularly FIG. 1 thereof, the apparatus comprises a diagnostic dish 1 secured on a holder 2 preferably in the form of a handle in which a valve 21 having a control lever 22 are provided.

Figure 2:
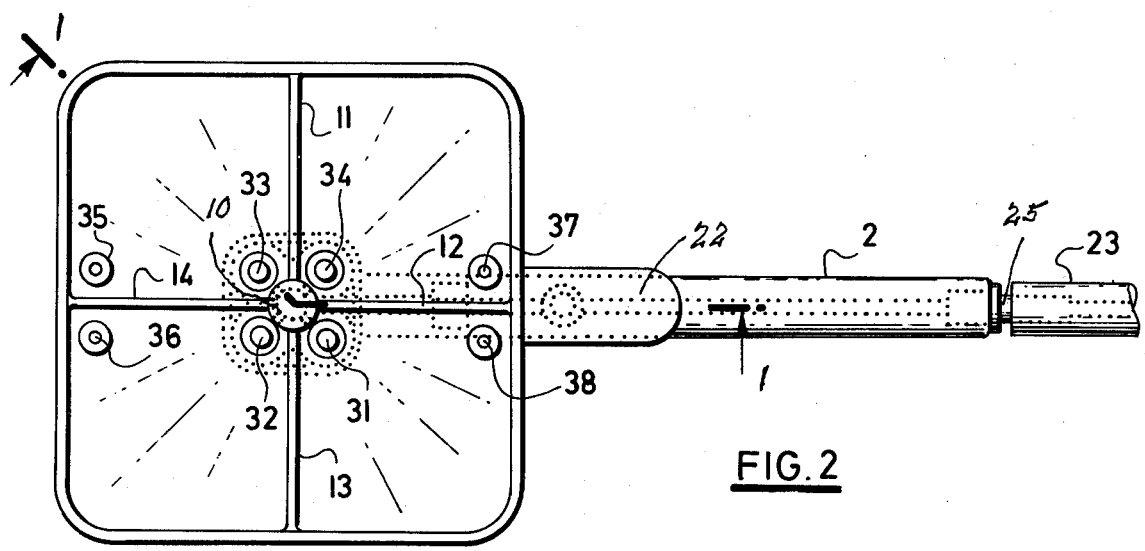
FIG. 2 is a view in plan of the apparatus shown in FIG. 1.

The holer 2 is attached, via a joint member 25, by means of a hose 23 to a supply (not shown) of scavenging liquid such as water. The diagnostic dish 1 is divided by vertical partition walls 11, 12, 13 and 14 into four identical diagnostic units. In the center of the diagnostic dish 1 there is disposed a body 10 receiving downwardly inclined scavenging nozzles 100 which are directed toward upwardly extending measuring probes 31, 32, 33 and 34 disposed in the lowermost portions of the bottoms of the respective diagnostic units. A passage 24 of the holder 2 discharges into a passage 24 a communicating with the passage in body 10. The diagnostic units are moreover provided with signal lights 35, 36, 37 and 38 as shown in FIG. 2.

Figure 3:
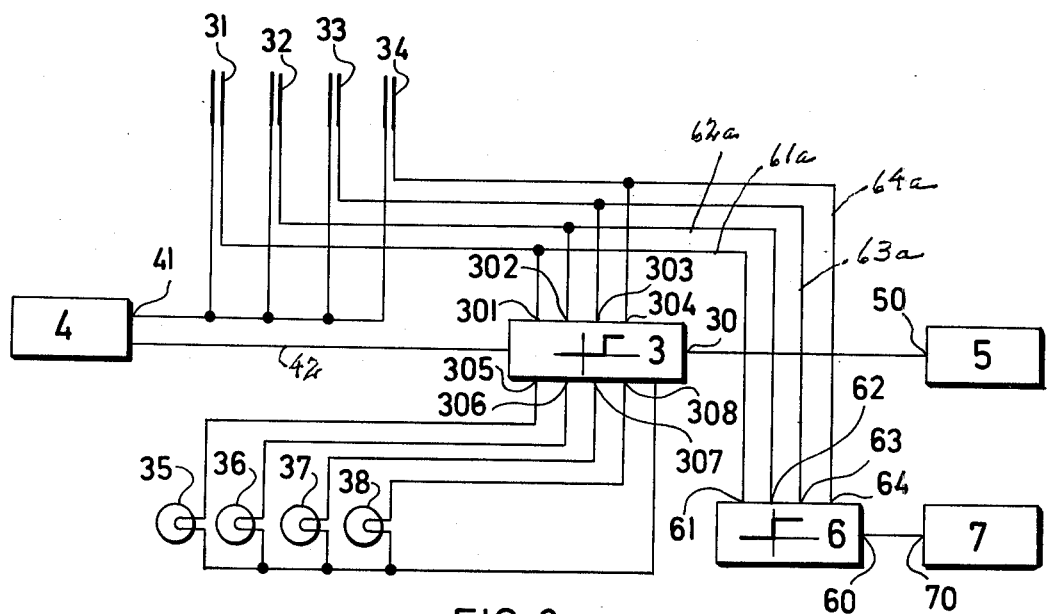
FIG. 3 is a block and wiring diagram of the apparatus as a whole.

FIG. 3 shows a block and wiring diagram of the apparatus as a whole, wherein the measuring probes 31, 32, 33 and 34 are embodied as electrodes enabling the electrical conductivity of milk in the respective diagnostic units to be measured.

The block diagram shown in FIG. 3 comprises a source of A.C. electric power such as an alternator 4, a milk quality evaluating circuit incorporated in a unit 3, a display 5 showing the diagnostic results of the tests on milk from the particular teats then under test, signal lights 35, 36, 37 and 38, a circuit 6 for monitoring the degree of filling of each diagnostic unit as indicated by the respective probes, and a display 7 for indicating the total number of examinations. As shown, one terminal 41 of alternator 4 is connected to one side of each of probes 31-34, incl. The other terminal of the alternator is connected to evaluating circuit 3 by a wire 43. The other side of each of probes 31-34, incl, is connected by respective wires 61a-64a, incl., to the monitoring circuit 6.

In operation, the milker, after having cleaned and dried the animal's teats, milks off the initial milk emission from each teat into the respective diagnostic unit.

After the measuring probes 31, 32, 33, and 34 have been flooded by milk, an alternate current of sinusoidal course and a suitable frequency flows from the terminal 41 of the alternator 41 through the probe flooding milk to inlets 301, 302, 303 and 304 of the milk quality evaluating circuit 3 and simultaneously to input terminals 61, 62, 63, 64 of the circuit 6 monitoring the degree of flooding of the measuring probe. The sensitivity of said monitoring circuit 6 is higher than that of the milk quality evaluating circuit 3; while the former indicates every milk specimen not corresponding to a standard, the latter responds to objectionable milk types only.

The number of examined teats is recorded by the display 7, to the input terminal 70 of which pulses are supplied from the output 60 of the circuit 6 for monitoring the degree of flooding of the measuring probe.

The number of unsatisfactory teats is recorded by the display 5, to the input terminal 50 of which pulses are supplied from the output 30 of the milk quality evaluating circuit 3.

If an adjusted sensitivity limit of the milk quality evaluating circuit 3 has been surpassed due to an increased milk conductivity, a signal is given by the respective one of the signal lights 35, 36, 37, 38 connected to the signal oulets 305, 306, 307, 308 of said circuit 3, and simultaneously the output 30 of said cirucit 3 emits a pulse to the input terminal 50 of the display 5.

The milker pours out the examined milk specimen and cleans the diagnostic dish 1 by opening valve 21, pressing down the control lever 22 on the holder 2, and puts the dish aside.

The afore-mentioned light signals give the milker objective information about the incapacity of the respective mammary gland to be emptied by the milking unit. The signal simultaneously gives the milker a command to seclude the cow from the other herd members and to hand it over to further veterinary medical examination, or treatment.

Another advantage of the apparatus according to the present invention resides in the possibility of continuous inspection of mammary gland health conditions by veterinary service member, and is of particularly value in a computerized and data processing process. The apparatus of the invention can be also applied as a unit of an automated system.

Although the invention is illustrated and described with reference to a single preferred enbodiment thereof, it is to be expressly understood that it is in no way limited by the disclosure of such a single preferred embodiment, but is capable of numerous modifications within the scope of the appended claims. Thus the measuring probes 31-34, incl., may operate on a principle other than the detection of the electrical conductivity of milk, such as the measuring of milk temperative by thermistor, measuring the sonic impedance of milk by supersonic waves, and the like.

What is claimed is:

1. In an apparatus for diagnosing disorders in the milk secretion of animals, said apparatus being based upon an electric detection of deviations of milk specimens from standard acceptable milk, the improvement comprising a holder carrying a diagnostic dish divided by partition walls into diagnostic units, the diagnostic units being provided with respective measuring probes, scavenging nozzles in the units directed toward the respective probes, and signal lights interconnected in a first circuit incorporating said probes for evaluating the quality of milk in the respective diagnostic units, the output of said circuit being connected to the input of a display indicating the quality of the milk specimen in each diagnostic unit.

2. Apparatus as claimed in claim 1, wherein the holder has a handle receiving scavenging liquid supply means and conductors for supplying power to the measuring probes and to the signal lights.

3. Apparatus as claimed in claim 1, wherein the measuring probes are arranged in the bottom portions of the diagnostic units, and the scavenging nozzles are disposed in a body situated between the measuring probes and connected via a valve to a scavenging liquid supply means.

4. Apparatus as claimed in claim 3, wherein the valve is controlled by a lever on the handle.

5. Apparatus as claimed in claim 1, wherein the milk quality evaluating circuit is parallel-connected with a second circuit for monitoring the quantity of milk in each of the diagnostic units, the second circuit being connected to a display for indicating the total number of examinations.

* * * * *